United States Patent
Joshi et al.

(10) Patent No.: US 9,801,918 B2
(45) Date of Patent: Oct. 31, 2017

(54) **METHODS OF TREATMENT USING EXTRACTS OF *ANISOMELES HEYNEANA***

(71) Applicant: Council of Scientific & Industrial Research, New Delhi (IN)

(72) Inventors: Swati Pramod Joshi, Maharashtra (IN); Roshan Rajan Kulkarni, Maharashtra (IN); Ketaki Dilip Shurpali, Maharashtra (IN); Sampa Sarkar, Maharashtra (IN); Dhiman Sarkar, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 15/168,643

(22) Filed: May 31, 2016

(65) Prior Publication Data

US 2016/0271196 A1 Sep. 22, 2016

Related U.S. Application Data

(63) Continuation of application No. 14/237,314, filed as application No. PCT/IB2012/001508 on Aug. 6, 2012, now abandoned.

(30) Foreign Application Priority Data

Aug. 5, 2011 (IN) .......................... 2222/DEL/2011

(51) Int. Cl.
*A61K 31/34* (2006.01)
*A61K 36/53* (2006.01)
*A61K 31/365* (2006.01)
*A61K 31/191* (2006.01)
*H01G 9/20* (2006.01)

(52) U.S. Cl.
CPC ............ *A61K 36/53* (2013.01); *A61K 31/191* (2013.01); *A61K 31/365* (2013.01); *H01G 9/2059* (2013.01); *A61K 2236/00* (2013.01); *A61K 2236/39* (2013.01); *H01G 9/2031* (2013.01); *Y02E 10/542* (2013.01)

(58) Field of Classification Search
CPC ....................................................... A61K 36/53
USPC ....................................................... 514/468
See application file for complete search history.

(56) References Cited

PUBLICATIONS

Renwick, et al. J. Chem. Soc. (C), 1968, 1949-1954, on p. 1950, No. 16 in Table 1).*
Tsuchiya Int. J. Cancer: 26, 171-176, 1980.*
Drexler et al. Leukemia (2003) 17, 416-426.*
Simeone in Cecil Textbook of Medicine, 20th ed. J.C. Bennett. Philadelphia: WB Saunders Co., 1996. Published as 1 volume.*
Freshney (Culture of Animal Cells, A Manual of Basic Technique, Alan R. Liss, Inc., 1983, New York, p. 4).*

* cited by examiner

*Primary Examiner* — Nizal Chandrakumar
(74) *Attorney, Agent, or Firm* — Shaukat A. Karjeker; Colin P. Cahoon; Carstens & Cahoon, LLP

(57) ABSTRACT

The present invention describes the use of pharmaceutical compositions including compounds of formula 2 (below) for treatment of infections related to *M. tuberculosis* and for anti-proliferative activity. Also, the present invention discloses a process of extraction of compounds of formula 2 from the extract of aerial parts of *Anisomeles heyneana*:

Formula 2

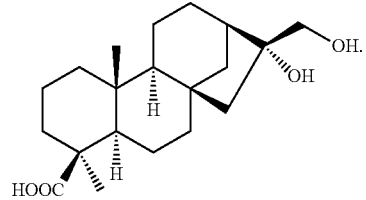

3 Claims, 5 Drawing Sheets

METHODS OF TREATMENT USING EXTRACTS OF *ANISOMELES HEYNEANA*

CROSS-REFERENCE TO RELATED APPLICATIONS

This application is a continuation of U.S. application Ser. No. 14/237,314, filed Feb. 5, 2014, entitled "Compounds from *Anisomeles Heyneana*," the technical disclosures of which are hereby incorporated herein by reference.

The following specification particularly describes the nature of the invention and the manner in which it is to be performed

TECHNICAL FIELD OF THE INVENTION

The present invention relates to the isolation and characterization of diterpene compound of formula 1, 2 and 3 from the extract of aerial parts of *Anisomeles heyneana* and their application in various industries. More particularly, the present specification describes a pharmaceutical composition comprising at least one compound selected from formula 1 and formula 2 along with pharmaceutically acceptable excipients for treatment of leukemia. Further, the present specification describes a pharmaceutical composition comprising compound of formula 1 along with pharmaceutically acceptable excipients for the treatment of M. Tuberculosis.

The present invention further relates to process for isolation and characterization of diterpene compound of formula 1, 2 and 3 from the extract of aerial parts of *Anisomeles heyneana*

In addition, the present invention further relates to compound of formula 3 useful for converting solar energy into electric current in dye sensitized solar cells.

BACKGROUND AND PRIOR ART OF THE INVENTION

*Anisomeles* (Family: Lamiaceae) is a genus of herbaceous or shrubby plants distributed from Africa to India, South East Asia to North East Australia and east from China to Philippines. Genus *Anisomeles* is represented in Maharashtra by three species viz. *A. heyneana*, *A. malabarica* and *A. indica* of which *A. heyneana* is endemic to Maharashtra. *A. malabarica* and *A. indica* have been examined chemically and found to contain cembrane diterpenes, triterpenes, flavonoids, etc. while there is no reported phytochemical work on *A. heyneana*.

High Performance Thin Layer Chromatography (HPTLC) method has been developed for the quantification of quercetin, β-sitosterol, stigmasterol, catechin and ovatodiolide present in *A. indica* and *A. malabarica*.

*Anisomeles indica* is used in folk medicine all over the India, where it has received widespread use as folk medicine, predominantly in the treatment of intestinal disorders and intermittent fever. *Anisomeles indica* has anti-microbial, astringent, carminative properties. Ethanolic extract (50%) of the herb showed hypothermic activity and when burnt, acted as a mosquito repellant. The essential oil present in the herb is useful in uterine affections, whereas, *Anisomeles malabarica* is useful in halitosis, epilepsy, hysteria, amnesia, anorexia, dyspepsia, colic, flatulence, intestinal worms, fever arising from teething children, intermittent fever, gout, swelling and diarrhea.

*Anisomeles heyneana*, commonly known as western hill catmint, is a tall, erect herb with slender stems with branches quadrangular having oppositely arranged ovate lance-like leaves. The flowers are white, tinged with pink, and 2-lipped.

Tuberculosis is a major and still neglected cause of death and disability with around 2 million deaths worldwide in 2009 and 9 million infections. There is more tuberculosis today than at any other time in History. The emergence of drug resistant strains and confluence with HIV epidemic has turned TB into a global public health crisis. Although, available drug regimens can cure most patients, emergence of MDR, SDR and XDR-TB coupled with insufficient global drug pipeline, justifies continued efforts towards development of new drugs with new mode of action and novel structures.

Taiwan Publication No. 201023966 employs water decoction cooking method and modern scientific isolation and purification technologies, with *Anisomeles indica* (L.) Kuntze stem as extraction material, to derive effective ingredients. However, Taiwan Application No. 20100120578 provides composition that contains ovatodiolide with effective dosage to inhibit *Helicobacter pylori* growth, wherein ovatodiolide is derived from dried leaves of *Anisomeles indica* (L.) Kuntze.

The extraction/isolation of cembrane type diterpenoid compounds from *Anisomeles indica* are known in the prior art; such as two cembrane type diterpenoid compounds, namely ovatodiolide and 4,5 epoxyovatodiolide isolated from *Anisomeles indica*, which exhibits selective antiplatelet aggregation activities toward collagen is disclosed in Journal of Natural Products 2008 July 71(7), 1207-1212, whereas the isolation of cembrane-type diterpenoid (ovatodiolide) extracted from the whole plants of *Anisomeles indica* and their anti-inflammatory activities is reported by Yerra Rao et al. in Journal of Ethnopharmacology 121, (2), 292-296. Biologically active macrocyclic diterpenoids such as 4,7-oxycycloanisomellic acid, 4-methylene-5-hydroxyovatodiolode and 4-methylene-5-oxoanisomelic acid from (*Anisomeles indica*,) together with ovatodiolide, 4-5 epoxyovatodiolide and anisomelic acid having cytotoxic activity and calcium antagonistic activity is described in Plant Med 1986; 52(1); 38-41. However extraction of ovatodiolide and other diterpenoids from dried aerial parts of *Anisomeles ovata* is reported in Journal of Natural Products 47, (6), 1052-1068, 1984. Work by Shahidul Alam et al. in Elsevier Fitoterapia, September 2000 71(5):574-6 relates to ovatodiolide, from *Anisomeles indica* and its anti-HIV activity.

Formulation containing macrocyclic diterpene-ovatodiolide isolated from the roots of *Anisomeles malabarica* is known in the art. Further the isolation of diterpenoid [16, 17-dihydroxy-16beta(−)kauran-19-oic acid] belongs to kaurane derivative from *Beyeria* species (Family: Euphorbiaceae) is disclosed by Fujita, Eiichi et al in Bulletin of the Institute for Chemical Research, Kyoto University (1966), 44(3): 239-272; whereas a oxygenated rare phyllocladane like phyllocladan-16a,19-diol along with flavonoids such as kaempferol-3-O-β-D-galactopyranoside, kaempferol-3-O-L-rhamnopyranoside and scopoletin, from the leaves of *Ailanthus triphysa* (Family: Simaroubaceae) is reported in Chinese Journal of Chemistry" 21, 2200-203, February 2003. Further the 13β-kaurane from *Plectranthus ambiguus* as inhibitors of the arachidonate metabolism and allergens is disclosed in Helvetica Chimica Acta-Vol. 86 (2003).

Leukemia is often referred to as cancer of the blood. It is characterized by the widespread uncontrolled proliferation of large numbers of abnormal blood cells, usually white blood cells, which take over the bone marrow and quickly spread to the blood stream. Other organs that may also be affected include lymph nodes, spleen, liver, central nervous system and other organs. As of 2010 there were an estimated 43,050 new cases of leukemia and 21,840 deaths due to leukemia. Everyday 118 people are diagnosed with leukemia and 60 of those lose the fight (http://www.leukemia-research.org/page.aspx?pid=214.

THP1 (Human acute monocytic leukemia cell line) is a well known model cell line to assess cytotoxic effects of drug candidates.

International Journal of Cancer Research 2007, 3 (4), 174-179 discloses study of the anticancer effect of crude ethanolic leaf extract of *Anisomeles malabarica*, which is evaluated on Diethylnitrosamine (DEN) in mice. The assessment of anticancer activity is evaluated by measuring the activities of total protein, Glutamate Pyruvate Transaminase (GPT), Glutamate Oxaloacetate Transaminase (GOT), Acid Phosphatase (ACP) and Alkaline Phosphatase (ALP) wherein the ethanolic extract at an oral dose of 100 mg kg$^{-1}$ is found to exhibit a significant (p<0.05) protective effect by reducing liver and serum levels of total protein, GPT, GOT, ACP and ALP as compared to DEN induced mice.

With regards to photosensitization technique, the solar energy is the most abundant, clean and green source of renewable energy and it can be harnessed via different routes in the interest of diverse applications. In many applications such as dye-sensitized solar cells (DSSCs), photocatalysis, solar to chemical conversion, etc., sensitizers with good optical properties over the visible range are essential. In the case of DSSCs, a number of factors such as the choice of the photoanode, the dye, the bottom, the counter electrodes, etc., can limit the cell performance, and a quantitatively significant stable electronic anchorage of the dye to the surface of the metal oxide nanostructure (e.g., TiO2, ZnO) is a critical factor that determines the cell efficiency. Among the various dyes that have been tested as sensitizers, ruthenium-based dyes have given the highest efficiency of ~11% on the laboratory scale. The main advantage of Ru-based dyes is their efficient metal to ligand charge transfer.

However, their high cost due to complex synthetic procedures as well as environmental hazards posed by the presence of heavy metals invite search for safer and cheaper alternatives. There have been interesting explorations of natural dyes in the context of the dye-sensitized solar cell (DSSC) application using pigments obtained from biomaterials such as flowers, fruits and leaves. The natural pigments commonly extracted from flowers and fruits are anthocyanins. Anthocyanins give colors ranging from red to blue depending on the pH of the medium. The maximum efficiency obtained by use of anthocyanins, i.e., juice obtained from *Hibiscus sabdariffa*, is 3.1%. The problem with anthocyanins is that they are pH sensitive, i.e., good binding with TiO2 occurs only if anthocyanin is present as flavylium ion species (which is stable) at pH around 1 to 3.2, but if pH is increased this ion gets hydrated to form quinoidal bases. These quinoidal compounds are labile and can be transformed into colorless compounds. If pH becomes more acidic <1 then the compound itself is leached out. Maintaining the right pH is nontrivial and at the same time a very crucial step while extracting anthocyanins. These anthocyanins are also thermally unstable. Porphyrins, which form the structural core of chlorophylls, the natural light harvesters, have also been examined as another class of sensitizers for DSSCs. Campbell et al. have synthesized metal-porphyrin dyes that show conversion efficiency of 7.1%. In 1994, M. Gratzel studied the mechanism of photosensitization of TiO2 solar cells by chlorophyll derivatives whereas, Kamat and co-workers in 1986 also explored the use of a chlorophyll analogue as a sensitizer for DSSCs. Natural chlorophyll extracted from Shiso leaves was used as sensitizer by Kumara et al., which showed efficiency of 0.59%. Isolated chlorophyll was used along with shisosin (an anthocyanin) to realize a synergistic effect that gave efficiency of 1.31%. Betalain pigments extracted from red beet root were also used as dyes sensitizer which gave efficiency of 0.19%. More recently, Wang and co-workers have done interesting studies on the chlorophyll system and have also modified the dye with metal conjugation to enhance efficiency.

Recenly, work by Shruti et al. in ACS Applied Materials and Interfaces (dx.doi.org/10.1021/am200341y) has demonstrated Isobutrin as a promising dye sensitizer in DSSCs. It belongs to chalcone class of natural products and in this work this class was reported first time as having potential to be developed as dye sensitizer.

Although a number of molecular sensitizers in the form of organic dyes (including heavy metal ion incorporated ones) have been synthesized and are being used, the corresponding methods of synthesis, application and prolonged use are not eco-friendly, cost-effective, with photo-, thermal-degradability dramatically reducing half life of sensitizer and hence affecting the coast and they may not be stable. It is therefore highly desirable to explore sources of new natural dye systems that are stable, nontoxic (biocompatible), and with the desirable optoelectronic properties.

In view of above drivers, uses and necessities of exploring natural products to supply respective leads, natural products like ovatodiolide, phyllocladane as well as phenolic compounds like verbascoside having different biological and physical properties can be isolated from different herbaceous plants. The existing diterpene compounds isolated from herbaceous plants do not exhibit such diverse applications as in the field of pharmaceutical, dye and solar energy.

Hence there is need to isolate and evaluate diterpenoids from the extract of *Anisomeles* species having biological activity such as anti-mycobacterial, anti-proliferative activity and solar cell sensitizing activity.

With due experiments the present inventors have succeeded to evaluate diterpenoids belonging to cembrane and phyllocladane class isolated from aerial parts of *Anisomeles heyneana* for significant anti-mycobacterial activity against M. tuberculosis and anti-proliferative activity against human Thp-1 cell line respectively.

The invention further provides another phenethylglycoside compound, verbascoside isolated from same species found to be effective dye-sensitizer in dye sensitized-solar cells (DSSCs).

Therefore, the objective of the present invention is to provide process for the isolation of non-toxic, economically viable and stable diterpenoids and phenethylglycoside isolated from extract of *Anisomeles heyneana*.

OBJECTS OF THE INVENTION

The main objective of the present invention is to provide pharmaceutical composition comprising at least one compound selected from formula 1 and formula 2 along with pharmaceutically acceptable excipients for the treatment of leukemia.

Another object of the present invention is to provide pharmaceutical composition comprising compound of formula 1 along with pharmaceutically acceptable excipients for the treatment of infections caused due to M. tuberculosis.

Yet another object of the present invention is to provide a process for isolation and characterization of diterpene compounds of formula 1, 2 and 3 from the extract of aerial parts of *Anisomeles heyneana* having diverse application in various industries.

Yet another object of the present invention is to provide compound of formula 3 useful for converting solar energy into electric current in dye sensitized solar cells.

BRIEF DESCRIPTION OF THE DRAWINGS

FIG. (1a) depicts $^1$HNMR spectra.
FIG. (1b) depicts $^{13}$CNMR spectra.
FIG. (1c) depicts DEPT spectra of compound of formula 1.
FIG. (2a) depicts $^1$HNMR spectra.
FIG. (2b) depicts $^{13}$CNMR spectra.
FIG. (2c) depicts DEPT spectra of compound of formula 2.
FIG. (3a) depicts $^1$HNMR spectra.
FIG. (3b) depicts $^{13}$CNMR spectra.
FIG. (3c) depicts DEPT spectra of compound of formula 3.

SUMMARY OF THE INVENTION

Figure 1A:
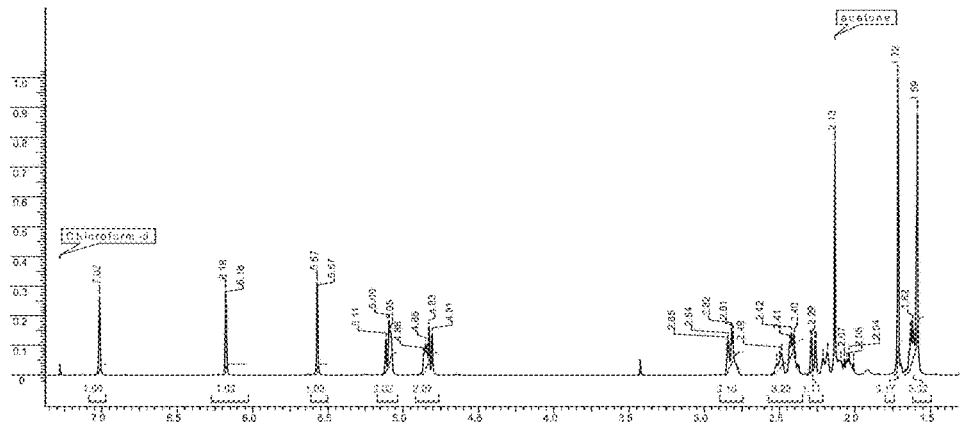
Figure 1B:
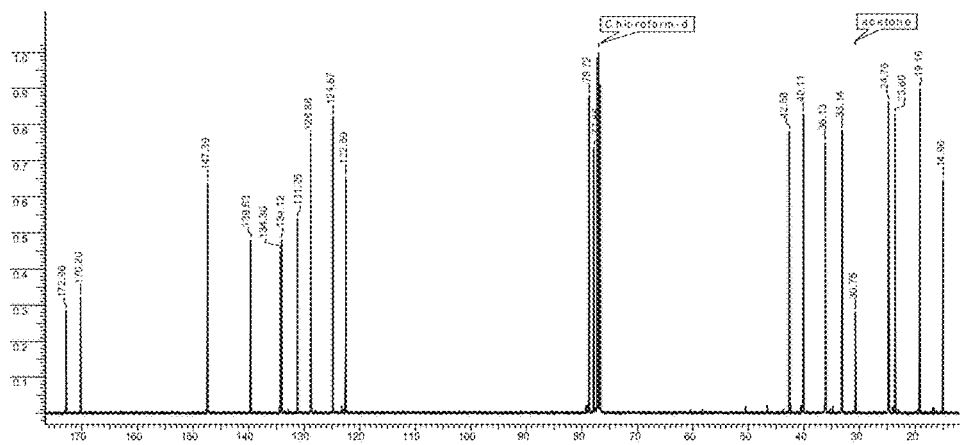
Figure 1C:
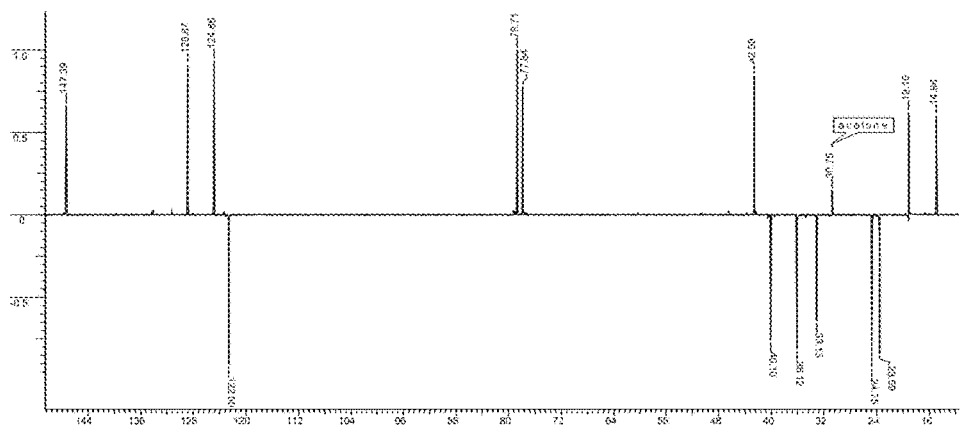
Figure 2A:
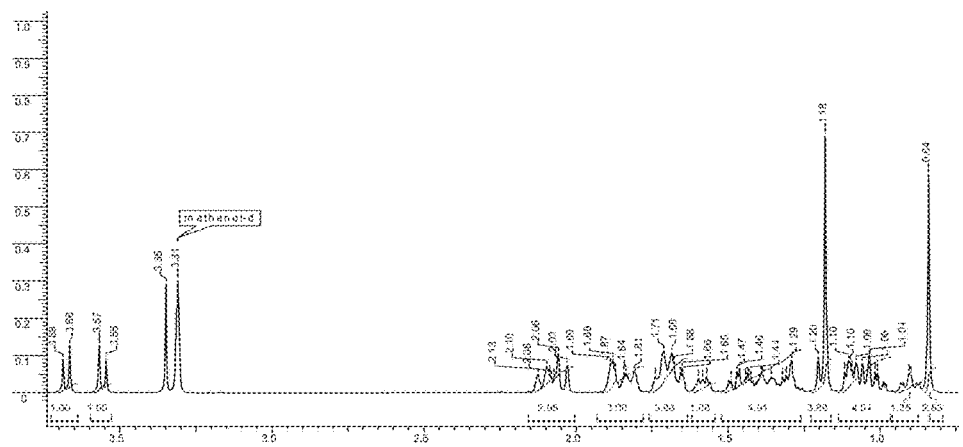
Figure 2B:
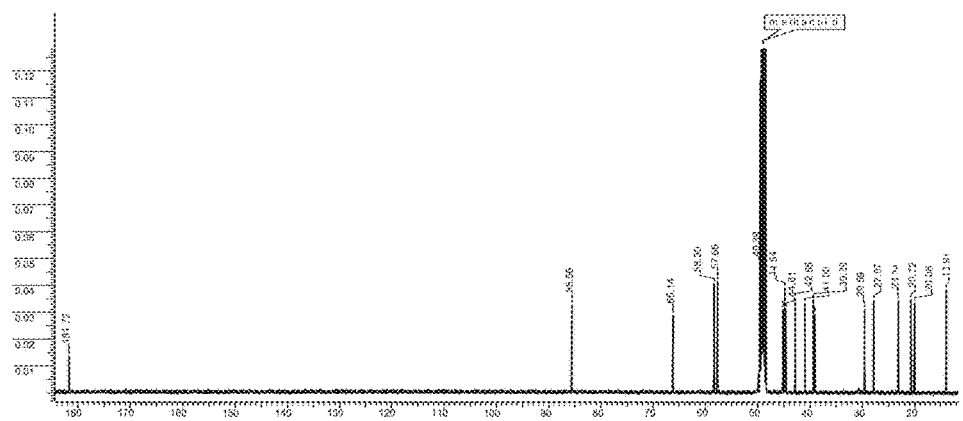
Figure 2C:
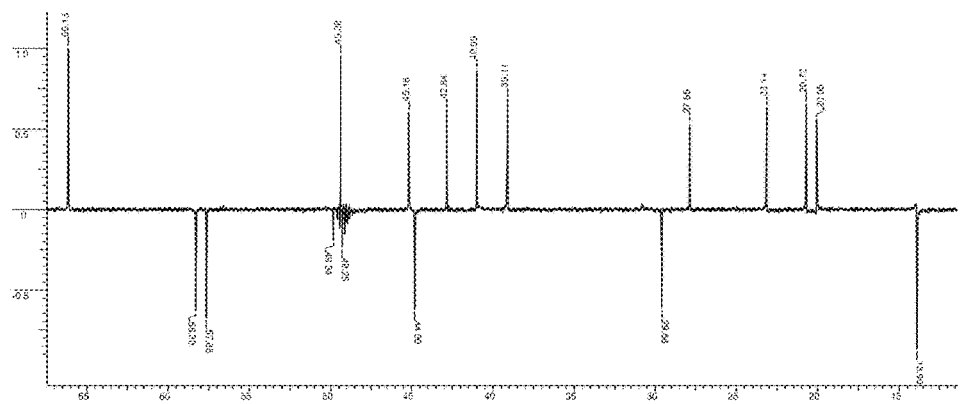
Figure 3A:
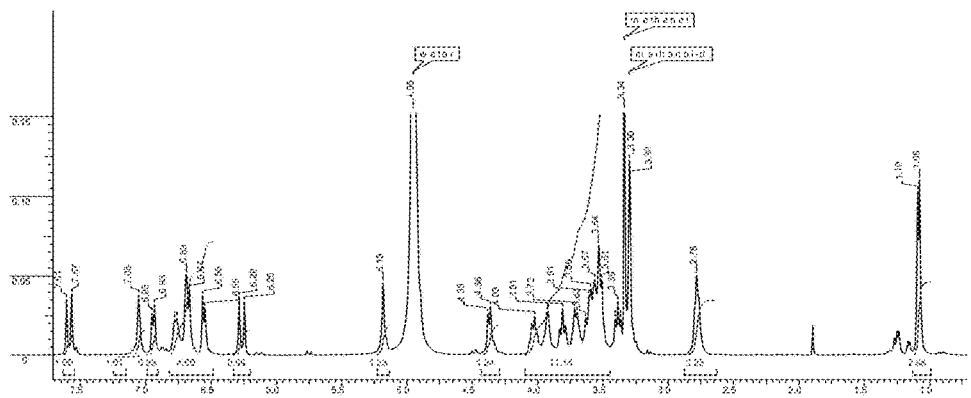
Figure 3B:
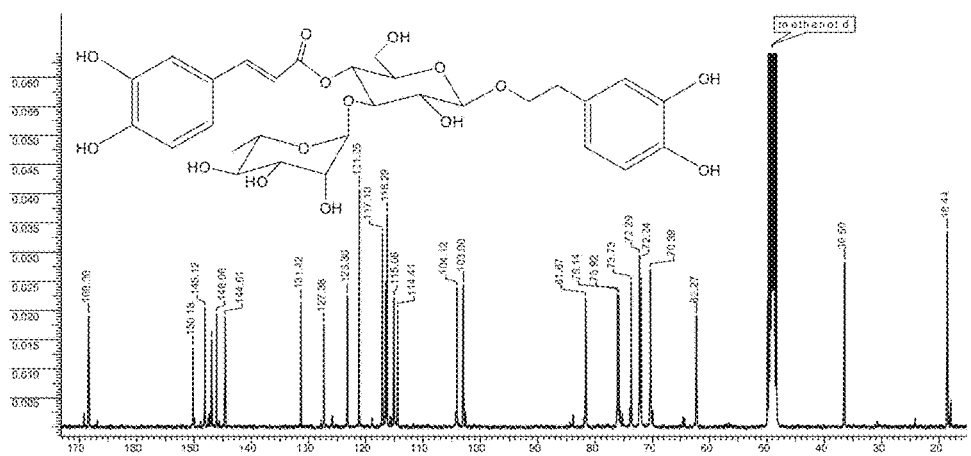
Figure 3C:
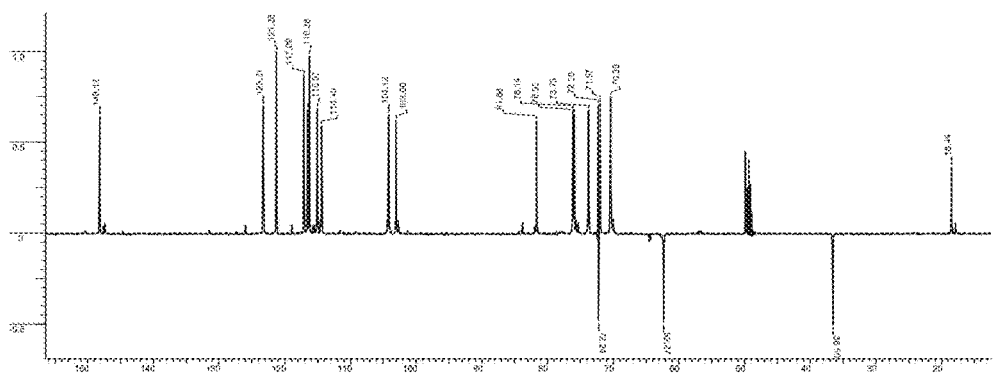

Accordingly, present invention provides pharmaceutical composition comprising at least one compound selected from formula 1 and formula 2 along with pharmaceutically acceptable excipients for anti proliferative activity.

Formula 1

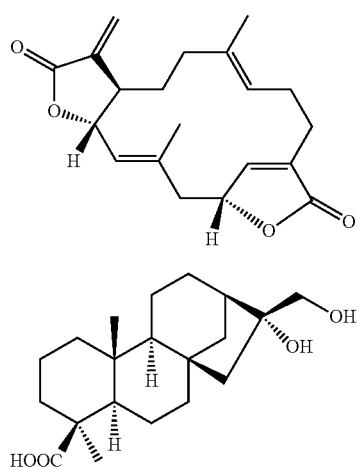

Formula 2

Additionally, the present invention provides a pharmaceutical composition comprising compound of formula 1 along with pharmaceutically acceptable excipients for the treatment of infections caused due to M. tuberculosis.

Further, the present invention provides a compound of formula 3 for the conversion of solar energy into electric current in dye sensitized solar cells.

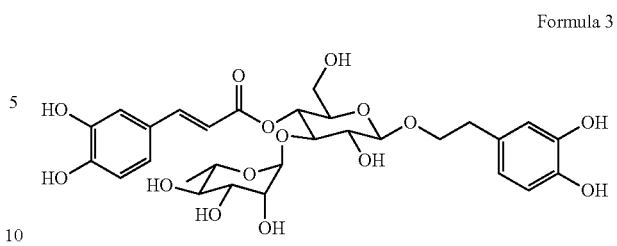

Formula 3

In yet another embodiment; present invention provides a process for isolation of compound of formula 1, formula 2 and formula 3 from the extract of aerial parts of *Anisomeles heyneana*

DETAILED DESCRIPTION OF THE INVENTION

Accordingly, the present invention relates to pharmaceutical composition comprising at least one compound selected from formula 1 and formula 2 along with pharmaceutically acceptable excipients for the treatment of leukemia.

The present invention further relates to pharmaceutical composition comprising compound of formula 1 along with pharmaceutically acceptable excipients for the treatment of infections caused due to M. tuberculosis.

The present invention further describes the use of compound of formula 3 for the conversion of solar energy into electric current in dye sensitized solar cells.

According to one aspect of the invention, the compound of formula 1 or formula 2 are present in the range of 0.1 to 99% w/w in the pharmaceutical composition.

According to yet another aspect, the pharmaceutically acceptable excipients are selected from the group comprising diluents, binders, lubricants, wetting agents, and disintegrants and their combinations thereof.

The pharmaceutically acceptable excipients are the excipients well known in the art and those which have been conventionally used in the formulation of various compositions.

Present invention also relates to process for the isolation of non-toxic, economically viable and stable diterpenoids of formula 1 and 2 and phenethyl cinnamoyl glycoside of formula 3 with solar cell sensitizing activity isolated from extract of *Anisomeles heyneana*.

In an aspect, the present invention provide process for isolation of non-toxic, cheap/cost-effective, stable, eco-friendly and biocompatible diterpenes from extract of aerial parts of *Anisomeles heyneana* plant, wherein the diterpene compounds are selected from the group consisting of cembrane(formula 1), phyllocladane(formula 2) exhibit substantial anti-mycobacteria and anti-proliferation activities respectively and phenethylglycoside (formula 3) which is effective in conversion of solar energy into electric current in dye-sensitized solar cells.

*Anisomeles heyneana*, the entire mature plants in flowering, are collected from Purandar fort area, District, Pune. A herbarium is deposited in Botanical Survey of India, Western Circle, Pune (Voucher No. SPJ5). Plant material is cleaned off adhering dust and unwanted plant material. Roots are separated and aerial parts are dried in shade and pulverized.

The present invention provides process for isolation of compounds of formula 1, 2 and 3 from the extract of aerial parts of *Anisomeles heyneana* plant comprising the steps of:

i. powdering aerial parts of *A. heyneana* followed by extraction with acetone at temperature in the range of 25 to 30° C., filtering acetone solubles and concentrating under reduced pressure at 50 to 100 mm of Hg to obtain a greenish acetone extract;
ii. separating the extract of step a) by using column chromatography (CC) with increasing polarity of the polar solvent to afford 18 fractions (AH-1 to AH-18);
iii. Subjecting Fraction AH7 to CC in acetonitrile: chloroform gradient from 2 to 10% to collect six fractions (AH7a-AH7f).
iv. Subjecting Fraction AH8 to CC in acetonitrile: chloroform gradient from 2 to 10% to collect eight fractions (AH8a-AH8h);
v. Combining Fractions AH8a, AH8b and AH7b based on similarity of their TLC profile and to obtain compound 1 (80 mg) after CC in 1 to 5% methanol in chloroform;
vi. subjecting fraction AH-11 of step ii) to column chromatography in 1 to 5% of methanol in chloroform to collect eleven fraction. Sub fraction 7, which is further subjected to column chromatography with 6% methanol in chloroform, to collect 8 fractions. Sub-fraction 2 subsequently purified by washing with chloroform to obtain compound 2 (14 mg) i.e. (phyllocladan-16α,17-dihydroxy-19-oic acid);
vii. subjecting fraction AH-14 of step b) to column chromatography in chloroform with acetonitrile from 5 to 50% gives fifteen fractions. Sub-fraction 11 is further subjected to preparative thin layer chromatography in 20-30% methanol in chloroform to afford brown amorphous powder of compound 3 (35 mg) i.e. verbascoside.

The chromatographic separation of diterpene compounds 1 and 2 and phenethylglycoside 3 from aerial parts of *A. heyneana* is disclosed in Scheme 1.

The diterpenoid compound 1 (ovatodiolide) isolated from extract of *A. heyneana* is belonging to class cembrane, having chemical name (1R,3E,5S,9R,12E)-3,12-Dimethyl-8-methylene-6,18-dioxatricyclo[14.2.1.05,9]nonadeca-3,12,16(19)-triene-7,17-dione and molecular formula $C_{20}H_{24}O_4$.

Compound of formula 1

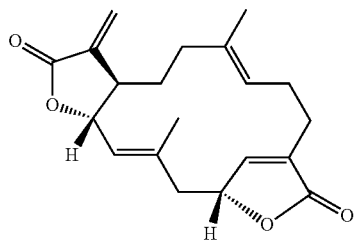

(Ovatodiolide)

chromatography in chloroform with acetonitrile from 2 to 10%. From fraction 8, sub-fractions 1 and 2 are pooled with sub-fraction 2 of fraction 7 from above column chromatography and compound 1 i.e. (ovatodiolide) is obtained from this pool after rechromatography in 2% methanol in chloroform.

The diterpenoid compound 2 (phyllocladan-16α,17-dihydroxy-19-oic acid) isolated from *A. heyneana* is belonging to phyllocladane class.

Compound of formula 2

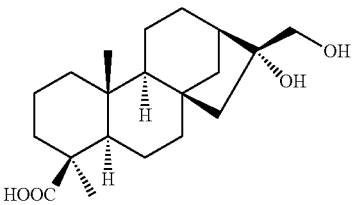

(Phyllocladan-16α, 17-dihydroxy-19-oic-acid)

18 fractions of *A. heyneana* are separated by column chromatography as described hereinabove, wherein fraction 11 is subjected to column chromatography in 3% methanol in chloroform to obtain sub-fraction 7 which is again subjected to column chromatography in 6% methanol in chloroform. From fraction 2 of this column, compound 2 i.e. (phyllocladan-16α,17-dihydroxy-19-oic acid) is precipitated as small crystals which are purified by washing with chloroform.

In another embodiment, the compound 3 (verbascoside) isolated from extract of *A. heyneana* is belonging to class phenethylglycoside, which is also known as TJC 160; Acetoside; Kusaginin; 2-(3,4-dihydroxyphenyl)ethyl 3-O-(6-deoxy-alpha-L-mannopyranosyl)-4-O-[(2E)-3-(3,4-dihydroxyphenyl)prop-2-enoyl]-beta-D-gluco pyrano side; beta-D-glucopyranoside, 2-(3,4-dihydroxyphenyl)ethyl 3-O-(6-deoxy-alpha-L-mannopyranosyl)-4-O-[(2E)-3-(3,4-dihydroxyphenyl)-1-oxo-2-propenyl] having molecular formula $C_{29}H_{36}O_{15}$.

Compound of formula 3

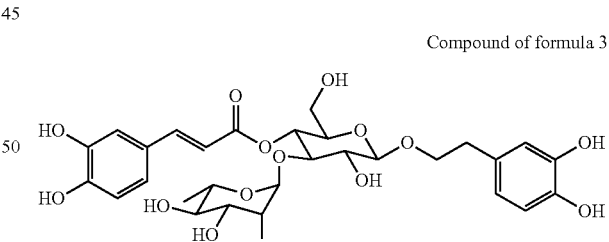

(Verbascoside)

According to the process of the present invention, the aerial parts of *A. heyneana* is powdered and extracted with acetone (3×3 L) for 14 hrs at room temperature 25 to 30° C., the mixtures is further filtered and concentrated under reduced pressure to obtain greenish acetone extract, which is then separated by using column chromatography (CC) with increasing polarity of acetone in petroleum ether to afford 18 fractions of *A. heyneana*. The fraction 7 is subjected to column chromatography in chloroform with acetonitrile from 2 to 10%. Also fraction 8 is subjected to column 18 fractions of *A. heyneana* are separated by column chromatography as described hereinabove, wherein fraction 14 is subjected to column chromatography in chloroform with acetonitrile from 5 to 50% to obtain sub-fraction 11, from which compound 3 i.e. (verbascoside) is isolated as brown amorphous powder after preparative thin layer chromatography in 25% methanol in chloroform.

The diterpenoid compound of formula 1 and compound of formula 2 are used for the preparation of pharmaceutical composition for anti-proliferative activity-MTT cell proliferation assay on human monocytic leukaemia Thp-1 cell lines. The diterpenoid compound 1 is used for the preparation of pharmaceutical composition having anti-tubercular activity. The effect of compound 1 and compound 2 on the viability of Thp-1 cell line at 100 μg/ml and $IC_{90}{}^b$ value against M. tuberculosis respectively is described herein below in Table 1.

TABLE 1

Effect of compounds 1 and 2 on the viability of Thp-1 cell line and *M. tuberculosis* bacilli.

| Compound | % Inhibition on Thp-1 cell line at 100 μg/ml | $IC_{90}{}^b$ value determined against *M. tuberculosis* (μg/ml) |
|---|---|---|
| 1 | 96.4 ± 0.4592 | 6.53 ± 0.893 |
| 2 | 59.02 ± 0.8725 | Not active[c] |
| Isoniazid | — | 0.05 ± 0.003 |
| Paclitaxel | 61% ± 0.501 | — |
| Vehicle Control[a] | No inhibition | No inhibition |

[a]1% Dimethyl sulfoxide (DMSO),
[b]Concentration of compounds exhibiting 90% inhibition against growth of *M. tuberculosis*.
[c]at 100 μg/ml The present invention provides a pharmaceutical composition comprising diterpenoid compound isolated from of *A. heyneana* consisting of at least one compound selected from the group ovatodiolide of formula 1 and phyllocladan-16α, 17-dihydroxy-19-oic acid of formula 1 together with at least one pharmaceutical acceptable excipient, useful in the treatment of mycobacterial tubercular infections and for leukemia. The pharmaceutical acceptable excipients are selected from diluents, binders, lubricants, wetting agents and disintegrant etc. Further the active ingredients and excipients can be formulated into compositions and dosage forms according to methods known in the art.

The pharmaceutical composition of the present invention may be formulated in form of tablets, capsules, pellets, granules, powder, suspension, syrup, liquid, intravenous, intramuscular injections, topical creams, ointments, gels, etc.

Figure 4:
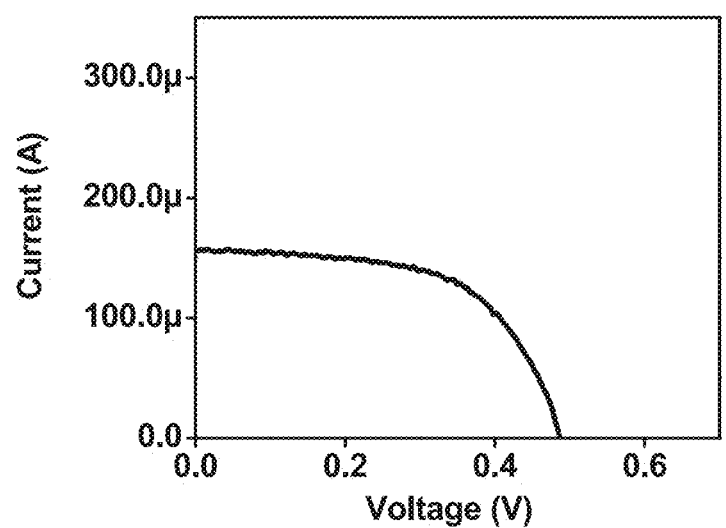
FIG. 4 depicts I-V (current vs voltage) plot for compound of formula 3.
Figure 5:
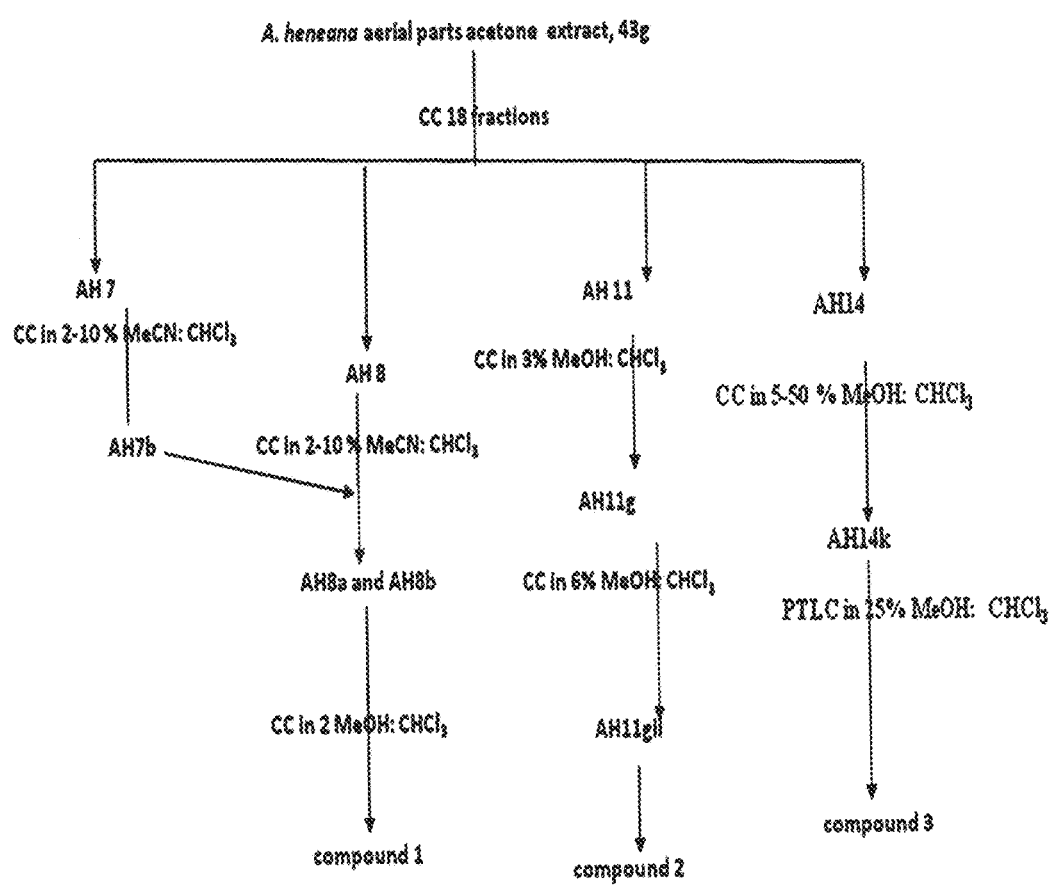
FIG. 5 is Scheme 1 representing a chromatographic separation of *A. heyneana*.

The compound 3 (verbascoside) is obtained from the fraction 14 of the *A. heyneana* extract of the present invention is found to be effective as dye-sensitizer in dye-sensitized solar cells (DSSCs), wherein solar energy is converted in electric current by using the doctor blading method. The conversion is carried out in the presence of electrolyte such as 0.5M to 0.8M 1 propyl-2,3-dimethyl-imidazolium iodide, 0.05 to 0.2 M LiI, 0.03 to 0.07 M $I_2$, and 0.3 to 0.6 M 4-tertbutylpyridine in acetonitrile. The I-V (current vs voltage) characteristics is measured which is depicted in FIG. 4 herein below. Further the measurements of the incident-photon-to-current conversion efficiency (IPCE) are performed by changing the excitation wavelength, and it is observed that compound 3 have ability to convert solar energy into electric energy, which subsequently gives 0.28% conversion efficiency which is described in Table 2 herein below.

TABLE 2

Solar cell properties of compound 3

| Sample | Voc (V) | Isc (mA) | FF (%) | Eff. (%) |
|---|---|---|---|---|
| 3 | 0.49 | 0.15 | 59.1 | 0.28 |

The compounds of the current invention isolated from *A. Heyneana* find use in various areas including, but not limited to therapeutics, herbicide, converting solar energy to electricity in dye sensitized solar cells.

In one embodiment, present invention provides a method of treating a subject in need of anti proliferative agent comprising administrating a pharmaceutical composition comprising the compound of formula 1 or compound of formula 2 along with pharmaceutically acceptable excipients.

In yet another embodiment, present invention provides a method of treating a subject suffering from mycobacterial tuberculosis infections comprising administrating a pharmaceutical composition comprising the compound of formula 1 along with pharmaceutically acceptable excipients.

In another embodiment of the present invention, compounds of formula 1 and 2 are useful for anti proliferative activity.

In yet another embodiment, compounds of formula 1 and 2 exhibit 59 to 97% inhibition on Thp-1 cell line at 100 μg/ml.

In yet another embodiment, compounds of formula 1 is useful for the treatment of infections caused due to M. tuberculosis.

In yet another embodiment, compound of formula 1 exhibit an $IC_{90}$ of 6.53±0.893 μg/ml in treatment of infections caused due to M. tuberculosis.

In yet another embodiment, compound of formula 3 is useful for the conversion of solar energy into electric current in dye sensitized solar cells.

In another embodiment of the present invention, compound of formula 3 exhibits 0.28% efficiency in conversion of solar energy into electric current in dye sensitized solar cells.

EXAMPLES

The following examples are given by the way of illustration and therefore should not be construed to limit the scope of the invention.

Example 1

Powdered aerial parts of *A. heyneana* (1.8 kg) were extracted with acetone (3×3 L, 14 h) at 27° C. temperature. The mixture was filtered and concentrated under reduced pressure to provide a greenish acetone extract (45.0 g). Acetone extract, (42.0 g), was separated by column chromatography (CC) with increasing polarity of acetone in petroleum ether to gave 18 fractions (AH1-AH18).

Example 2

Fraction AH7 (1.8 g) was subjected to column chromatography in chloroform with acetonitrile from 2 to 10%. Fraction AH8 (5.2 g) was subjected to column chromatography in chloroform with acetonitrile from 2 to 10%. From fraction 8, sub-fractions 1 and 2 were pooled with sub-fraction 2 of fraction 7 from above column chromatography and compound 1 was obtained from this pool after rechromatography in 2% methanol in chloroform (80 mg).

Example 3

Fraction AH11 (3.4 g) was subjected to column chromatography in 3% methanol in chloroform. Sub-fraction 7 was again subjected to column chromatography in 6% methanol in chloroform. From fraction 2 of this column, compound 2 was precipitated as small crystals (14 mg) which were purified by washing with chloroform.

Example 4

Fraction AH14 (15.6 g) was subjected to column chromatography in chloroform with acetonitrile from 5 to 50%. From sub-fraction 11, compound 3 was isolated as brown amorphous powder (25 mg) after preparative thin layer chromatography in 25% methanol in chloroform.

Example 5

Anti-Mycobacterial Activity

Compounds 1 and 2 were evaluated for their inhibition on M. tuberculosis by following an established protocol published earlier using isoniazid as positive control. The compound 1 exhibited anti-mycobacterial activity with $IC_{90}$ of 6.53 μg/ml.

Example 6

Anti Proliferative Activity-MTT Cell Proliferation Assay on Human Thp-1 Cell Line Compounds 1 and 2 were tested for their inhibitory effect on Thp-1 cells. About 10,000 cells were taken per well in 96-well tissue culture plates and treated with test samples at 100 μg/ml for 72 h. Vehicle control (DMSO, 1%) and positive control (Paclitaxel, 100 μg/ml) was run simultaneously. Cell proliferation was assessed with 10 μl samples from 5 mg/ml stock solution of tetrazolium salt (MTT) was dissolved in cell culture medium and subsequently incubated for additional 1 h at 37° C., 5% of $CO_2$ and 95% humidity in incubator. The violet coloured formazan crystals formed were solubilized in 200 μl of isopropanol and incubated for another 4 h. The optical density was read on a micro plate reader (Spectramax plus384 plate reader, Molecular Devices Inc) at 490 nm filter against a blank prepared from cell-free wells. Absorbance given by cells treated with the carrier DMSO alone was taken as 100% cell growth. All experiments were performed in triplicate, and the quantitative value was expressed as the average±standard deviation (as shown in Table 1).

Example 7

Solar Cell Sensitizing Activity

Fabrication and Testing of DSSCs. To make and study the DSSC solar cells, present inventors were employed a doctor blading method. After making the films they were annealed at 450° C. for 30 min. For sensitization, the films were dipped in solution of verbascoside for 24 h at room temperature (in separate experiments) and also with 0.5 mM N719 dye in ethanol for comparison. The samples were then rinsed with methanol to remove excess dye on the surface and air-dried at room temperature. This was followed by redox electrolyte addition and top contact of Pt coated FTO. The electrolyte used was 0.6M 1-propyl-2,3-dimethyl-imidazolium iodide, 0.1 M LiI, 0.05 M 12, and 0.5 M 4-tert-butylpyridine in acetonitrile.27 The I-V characteristics were measured under exposure with 100 mW/cm$^2$ (450W xenon lamp, Newport Instruments), 1 sun AM 1.5, simulated sunlight as a solar simulator. The current was measured using a Kiethley 2400 source. Measurements of the incident-photon-to-current conversion efficiency (IPCE) were performed by changing the excitation wavelength (Newport Instruments).

The compound 3 was evaluated for its ability to convert solar energy into electric current in dye sensitized solar cells. It gave 0.28% conversion efficiency (FIG. 4: voltage vs current plot for compound 3).

Examples 8-21 Examples of Pharmaceutical Composition

Example 8

Composition

| | |
|---|---|
| Phyllocladan-16α,17-dihydroxy-19-oic acid | 10.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and fill in pouch or bottle.

Mode of administration:

Disperse the powder in water/juice.

Example 9

Composition

| | |
|---|---|
| Phyllocladan-16α,17-dihydroxy-19-oic acid | 20.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and fill in pouch or bottle.

Mode of administration:

Disperse the powder in water/juice.

Example 10

Composition

| | |
|---|---|
| Phyllocladan-16α,17-dihydroxy-19-oic acid | 10.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and may be filled in a capsule of suitable size.

Mode of administration: The capsule may be had with water of juice

Example 11

Composition

| | |
|---|---|
| Phyllocladan-16α,17-dihydroxy-19-oic acid | 20.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and may be filled in a capsule of suitable size.

Mode of administration;

Mode of administration: The capsule may be had with water of juice

Example 12

Composition

| | |
|---|---|
| Phyllocladan-16α,17-dihydroxy-19-oic acid | 10.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and may be compressed as tablet.

Mode of administration;

Mode of administration: The tablet may be taken with water or juice

Example 13

Composition

| | |
|---|---|
| Phyllocladan-16α,17-dihydroxy-19-oic acid | 5.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and may be compressed as tablet.

Mode of administration: The tablet may be taken with water or juice

Example 14

Composition

| | |
|---|---|
| Phyllocladan-16α,17-dihydroxy-19-oic acid | 5.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and fill in pouch or bottle.

Mode of administration:

Disperse the powder in water/juice.

Example 15

Composition

| | |
|---|---|
| Ovatodiolide | 10.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and fill in pouch or bottle.

Mode of administration:

Disperse the powder in water/juice.

Example 16

Composition

| | |
|---|---|
| Ovatodiolide | 20.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and fill in pouch or bottle.

Mode of administration:

Disperse the powder in water/juice.

Example 17

Composition

| | |
|---|---|
| Ovatodiolide | 10.0% w/w |
| Color Amaranth | 0.3% w/w |
| Raspberry Flavor | 0.7% w/w |

| | |
|---|---|
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and may be filled in a capsule of suitable size.

Mode of administration: The capsule may be had with water of juice

Example 18

Composition

| | |
|---|---|
| Ovatodiolide | 20.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and may be filled in a capsule of suitable size.

Mode of administration;

Mode of administration: The capsule may be had with water of juice

Example 19

Composition

| | |
|---|---|
| Ovatodiolide | 10.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and may be compressed as tablet.

Mode of administration;

Mode of administration: The tablet may be taken with water or juice

Example 20

Composition

| | |
|---|---|
| Ovatodiolide | 5.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and may be compressed as tablet.

Mode of administration: The tablet may be had with water of juice

Example 21

Composition

| | |
|---|---|
| Ovatodiolide | 5.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and fill in pouch or bottle.

Mode of administration:

Disperse the powder in water/juice.

The structures of compounds 1, 2 and 3 were elucidated using $^1$H NMR and $^{13}$C NMR.

TABLE 3

$^1$H NMR and $^{13}$C NMR data for compound 1 (in $CDCl_3$)

| No. | $^{13}$C (δ) | $^1$H (δ) |
|---|---|---|
| 1 | 42.58 | 2.42(m)** |
| 2 | 23.60 | 2.83(m), 2.12(m) |
| 3 | 24.76 | 2.5(m), 2.42(m) |
| 4 | 131.25 | — |
| 5 | 124.87 | 4.85 (bt, 5.69) |
| 6 | 33.14 | 1.64(m) |
| 7 | 36.13 | 2.19(d, 14.61), 2.04(m) |
| 8 | 139.63 | — |
| 9 | 147.39 | 7.02(bs) |
| 10 | 77.85 | 4.81 (dd, 10.17, 1.42) |
| 11 | 40.11 | 2.84(dd, 10.34, 3.61), 2.29(dd, 10.41, 3.65) |
| 12 | 134.12 | — |
| 13 | 128.88 | 5.10(d, 10.43) |
| 14 | 78.72 | 5.08 (bs) |
| 15 | 134.30 | — |
| 16 | 172.96 | — |
| 17 | 122.59 | 5.57(d, 1.5), 6.18(d, 1.5) |
| 18 | 14.96 | 1.59(bs) |
| 19 | 170.20 | — |
| 20 | 19.16 | 1.72 (d, 0.88) |

TABLE 4

$^{13}$C and $^1$H NMR data of compound 2: (in $CD_3OD$)

| | 2 (in $CD_3OD$) | |
|---|---|---|
| No | $δ_H$ (J in Hz) | $δ_C$ |
| 1 | 1.70 (eq)*, 0.89 dt (4.1, 13.3) (ax)* | 41.0 |
| 2 | 1.37 m (eq), 1.86 m (ax) | 20.1 |
| 3 | 2.11m (eq), 1.00m (ax) | 39.1 |
| 4 | — | 44.6 |
| 5 | 1.08m | 58.3 |
| 6 | 1.83m (eq), 1.70m (ax) | 23.1 |
| 7 | 1.66 m, 1.46 dt (3.78, 13.45) | 42.8 |
| 8 | — | 44.9 |
| 9 | 1.1m | 57.7 |
| 10 | — | 39.4 |
| 11 | 1.59m(eq), 1.31m(ax) | 20.7 |
| 12 | 1.71m (eq), 1.43m (ax) | 27.9 |
| 13 | 1.88m | 44.8 |

TABLE 4-continued

<sup>13</sup>C and <sup>1</sup>H NMR data of compound 2: (in CD$_3$OD)

| | 2 (in CD$_3$OD) | |
|---|---|---|
| No | $\delta_H$ (J in Hz) | $\delta_C$ |
| 14 | 2.10m, 1.04m | 49.4 |
| 15 | 2.04 d (11) (eq), 1.19 bd (11) (ax), | 45.2 |
| 16 | — | 85.6 |
| 17 | 3.67 d (11), 3.56 d (11), | 66.1 |
| 18 | 1.18 s | 29.6 |
| 19 | — | 181.7 |
| 20 | 0.84 s | 13.9 |

TABLE 5

<sup>1</sup>H NMR and <sup>13</sup>C NMR data for compound 3 in (CD$_3$OD)

| | <sup>13</sup>C | <sup>1</sup>H |
|---|---|---|
| Caffeoyl | | |
| 1 | 131.42 | — |
| 2 | 117.10 | 6.68 m |
| 3 | 146.06 | — |
| 4 | 144.61 | — |
| 5 | 116.29 | 6.68 m |
| 6 | 121.25 | 6.56 bd (7.4) |
| 7 | 36.50 | 2.79 bt (9.5) |
| 8 | 72.24 | 4.03 q (8.56), 3.72 q (7.8) |
| Gucose | 104.12 | 4.38 d (7.58) |
| | 76.14 | 3.4 bt (8.31) |
| | 81.67 | 3.82 t (9.0) |
| | 70.39 | 4.94 o |
| | 75.92 | 3.6-3.5 m |
| | 62.27 | 3.6-3.5 m |
| Rhamnose | 103.00 | 5.19 bs |
| | 72.29 | 3.93 bs |
| | 71.98 | 3.6-3.5 m |
| | 73.73 | 3.30 o |
| | 70.48 | 3.6-3.5 m |
| | 18.44 | 1.09 d(6.1) |
| Cinnamoyl | | |
| 1' | 127.38 | |
| 2' | 115.08 | 7.06 bs |
| 3' | 150.18 | — |
| 4' | 146.94 | — |

TABLE 5-continued

<sup>1</sup>H NMR and <sup>13</sup>C NMR data for compound 3 in (CD$_3$OD)

| | <sup>13</sup>C | <sup>1</sup>H |
|---|---|---|
| 5' | 116.53 | 6.79 d(7.09) |
| 6' | 123.30 | 6.95 bd (7.58) |
| 7' | 148.12 | 7.6 d(15.9) |
| 8' | 114.41 | 6.275 d(15.9) |
| 9' | 168.36 | |

ADVANTAGE OF THE INVENTION

The compounds isolated are active against proliferative cells

The compounds isolated are active against *mycobacterium* infection

The invention has applications in solar cell.

Compound 2 has anti proliferative activity comparable to well known drug, paclitaxel.

We claim:

1. A method of inhibiting cell proliferation in human Thp-1 cell line by administering to the cell a composition of a compound extracted from *Anisomeles heyneana* of formula:

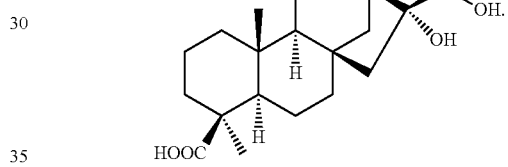

2. The method of claim 1, wherein the compound of the formula is present in the range of 0.1 to 99% w/w of the pharmaceutical composition.

3. The method of claim 1, wherein the pharmaceutical composition further comprises a pharmaceutically acceptable excipient is selected from the group comprising diluents, binders, lubricants, wetting agents, disintegrants and combinations thereof.

* * * * *